June 4, 1940. I. NAKATA ET AL Plant Pat. 401
CHRYSANTHEMUM
Filed Dec. 9, 1939
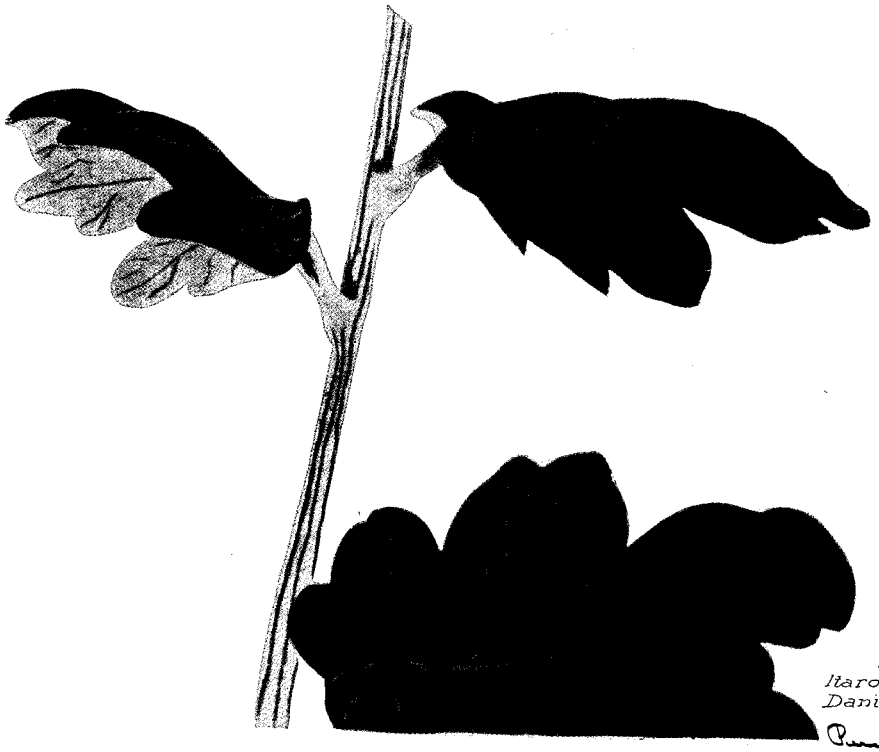
INVENTORS
Itaro Nakata
Daniel Nakata
ATTORNEY Patented June 4, 1940

Plant Pat. 401

UNITED STATES PATENT OFFICE

401

CHRYSANTHEMUM

Itaro Nakata and Daniel Nakata, Tracy, Calif.

Application December 9, 1939, Serial No. 308,443

1 Claim. (Cl. 47—60)

This discovery relates in general to chrysanthemums, and in particular is directed to a new and distinct variety of the large single mum of the type having a polypetalous corolla. The essential novel features of such new variety of chrysanthemum reside in the flower; the flower being extremely large and upright with rich, pure yellow petals. The flowers are, on the average, eight to nine inches in diameter, and have excellent lasting and shipping qualities without drooping.

Additional novel features of this new variety of chrysanthemum are the high or strong fragrance of the flowers and the strong stem with large clean cut leaves of dark green color.

Such new variety of chrysanthemum was discovered in the following manner:

In the fall of 1934 a late semi-double (spider variety) of tubular petaled chrysanthemum was cross pollinated to an early wild chrysanthemum; this being accomplished by removing the first set of buds from the wild variety which caused the sucker branch thereof to flower at a date late enough for cross pollination with the late variety. The wild variety thereafter produced approximately five thousand seeds which were set out in flats in the spring of 1935. Those of the seeds which germinated were transplanted into pots for initial growth and subsequently replanted in the ground.

In October 1935 substantially all of the above plants were in bloom and from these we selected those which appeared to be of any commercial value and which numbered approximately two hundred and fifty plants. Beginning in February 1936 the selected plants were propagated from cuttings and when such cuttings came into bloom in October 1936, one thereof had a large greenish-white single flower which had long coarse tubular petals, and whose petals drooped when the flower was open. Cuttings from such plant were rooted, transplanted, and in the fall of 1937 came into bloom.

One of the plants from such cuttings, and caused as the result of a sport, bore extremely large diameter, single, upright flowers having petals which were of a rich, pure yellow color. This was recognized as a new variety and is that variety which is herein described and claimed. Such variety has been successfully asexually reproduced and the reproduced plants bear flowers having characteristics identical with the parent plant. The discovery of such new variety was made at our nursery in the city of Tracy, California, and it is at such nursery that the variety has been successfully reproduced.

The accompanying drawing is a perspective view of a leaved stem bearing a flower of the new variety.

We refer now in some detail to the characteristics of such new variety and its flower.

The roots of the plant are perennial and the root system is strong. The stem of the plant is medullary or pithy with a wooly external surface of relatively dark green color; the stem being upright and strong.

The leaves are large and clean cut, dark green in color and amplexicaul, and the margins oval to lanceolate with a sinuate to serrate form of notches and wide openings.

The leaves remain much cleaner than other varieties and are thus less subject to attack by plant disease.

The flowers of the herein described variety may be classified by the Linnaean system as *Syngenesia superflua;* i. e., numerous individual florets clustered together on a common receptacle and surrounded or supported by an involucrum. The involucrum is imbricated and of the same general color and wooliness as the stem.

The disc florets on the expanded surface of the receptacle each consist of a tube, and a germen or ovary, which when ripe, forms the seed; the tube being disposed on and projecting from such ovary. The stamens are attached to the inside of the tube just below the mouth thereof; their anthers being adherent by their edges and having small membraneous appendages at the tip. The style of the pistil is regarded as filiform, and at its upper summit is split into two linear spreading parts or stigmas.

The enlarged ray florets, or radius of the receptacle, form a polypetalous corolla which comprises sixteen petals. Each petal is a large, pure yellow of delicate shade, and when the plant is grown with each plant having only a single large flower by reason of budding, the individual petals are approximately four inches in length. Such individual petals are longitudinally cupped, and curve upward slightly at the tip. These projecting petals are strong and sturdy, and the corolla is upright as distinguished from a drooping type.

In summary, the novel features of the new variety, and particularly of the flower, are its upright polypetalous corolla which holds out well and does not droop, and the long, pure yellow petals longitudinally cupped, and curved upward slightly at the tips. The flowers of the new variety are superb and attractive for use as cut flowers, and as the lasting and shipping qualities thereof are excellent, the flowers are admirably suited for propagation as a florist's item.

The chrysanthemum plant and its flower above described may, of course, vary in certain details depending on the soil and climatic conditions under which it is propagated.

Having thus described our discovery, we claim:

A chrysanthemum characterized by a flower having a large upright polypetalous corolla; the petals thereof being a rich, pure yellow color, long, sturdy, longitudinally cupped, and curved upward slightly at the tips.

ITARO NAKATA.
DANIEL NAKATA.